US010952610B2

(12) United States Patent
Ogino et al.

(10) Patent No.: US 10,952,610 B2
(45) Date of Patent: Mar. 23, 2021

(54) PORTABLE BIOLOGICAL SIGNAL MEASUREMENT/TRANSMISSION SYSTEM

(75) Inventors: Hirokazu Ogino, Tokyo (JP); Takaya Arimitsu, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 635 days.

(21) Appl. No.: 13/015,096

(22) Filed: Jan. 27, 2011

(65) Prior Publication Data

US 2011/0184255 A1 Jul. 28, 2011

(30) Foreign Application Priority Data

Jan. 27, 2010 (JP) .............................. JP2010-015345

(51) Int. Cl.
*A61B 5/00* (2006.01)

(52) U.S. Cl.
CPC .......... *A61B 5/0002* (2013.01); *A61B 5/6838* (2013.01); *A61B 5/7203* (2013.01); *A61B 5/7235* (2013.01); *A61B 5/747* (2013.01)

(58) Field of Classification Search
None
See application file for complete search history.

(56) References Cited

U.S. PATENT DOCUMENTS

| | | | |
|---|---|---|---|
| 4,784,162 A | 11/1988 | Ricks et al. | |
| 5,226,431 A | 7/1993 | Bible et al. | |
| 6,198,394 B1 * | 3/2001 | Jacobsen et al. | 340/573.1 |
| 2002/0161291 A1 | 10/2002 | Kianl et al. | |
| 2002/0161308 A1 | 10/2002 | Matsumura et al. | |
| 2004/0059205 A1 | 3/2004 | Carlson et al. | |
| 2004/0130446 A1 * | 7/2004 | Chen et al. | 340/539.12 |
| 2004/0199056 A1 * | 10/2004 | Husemann et al. | 600/300 |
| 2006/0025663 A1 | 2/2006 | Talbot et al. | |
| 2006/0094936 A1 * | 5/2006 | Russ | 600/300 |
| 2006/0122466 A1 | 6/2006 | Nguyen-Dobinsky et al. | |
| 2006/0129356 A1 | 6/2006 | Nakamoto et al. | |
| 2006/0282021 A1 * | 12/2006 | DeVaul et al. | 600/595 |
| 2007/0027367 A1 * | 2/2007 | Oliver et al. | 600/300 |
| 2007/0179734 A1 * | 8/2007 | Chmiel et al. | 702/127 |
| 2008/0215360 A1 * | 9/2008 | Dicks et al. | 705/2 |
| 2008/0281168 A1 | 11/2008 | Gibson et al. | |

(Continued)

FOREIGN PATENT DOCUMENTS

| | | |
|---|---|---|
| CN | 101491431 A | 7/2009 |
| CN | 101536900 A | 9/2009 |

(Continued)

OTHER PUBLICATIONS

Japanese Office Action for the related Japanese Patent Application No. 2010-015345 dated Jul. 29, 2013.

(Continued)

*Primary Examiner* — Lindsey G Wehrheim
(74) *Attorney, Agent, or Firm* — Pearne & Gordon LLP

(57) ABSTRACT

A portable biological signal measurement/transmission system includes: a body unit; and at least one biological signal processing unit detachably connected to the body unit, and including a signal processor which processes a biological signal, the biological signal processing unit including a first transmitter which transmits the biological signal to the body unit when the biological signal processing unit is connected to the body unit.

26 Claims, 13 Drawing Sheets

(56) References Cited

U.S. PATENT DOCUMENTS

| | | | |
|---|---|---|---|
| 2009/0118595 A1* | 5/2009 | Greiner | A61B 5/0006 600/301 |
| 2010/0211713 A1* | 8/2010 | Waldhoff | A61B 5/0002 710/303 |
| 2011/0152632 A1* | 6/2011 | Le Neel et al. | 600/300 |

FOREIGN PATENT DOCUMENTS

| | | |
|---|---|---|
| CN | 201320165 Y | 10/2009 |
| DE | 10 2004 007 712 A1 | 10/2005 |
| JP | 4-371135 A | 12/1992 |
| JP | 2001-4453 A | 1/2001 |
| JP | 2002-224054 A | 8/2002 |
| JP | 2003-10138 A | 1/2003 |
| JP | 2005-538784 A | 12/2005 |
| JP | 2008-526443 T | 7/2008 |
| JP | 2008-229274 A | 10/2008 |
| JP | 2009-189570 A | 8/2009 |
| JP | 2010-12335 A | 1/2010 |
| WO | WO89/00024 A1 | 1/1989 |
| WO | 2004/026126 A1 | 4/2004 |
| WO | 2006/020212 A2 | 2/2006 |
| WO | 2009/052704 A1 | 4/2009 |

OTHER PUBLICATIONS

Partial European Search Report dated Jun. 17, 2011.
European Search Report for related European patent application 11152354.4 dated Dec. 14, 2011.
Japanese Office Action for the related Japanese Patent Application No. 2010-015345 dated Dec. 3, 2013.
Chinese Office Action for the related Chinese Patent Application No. 201110030382.9 dated Dec. 5, 2013.
Japanese Office Action for the related Japanese Patent Application No. 2010-015345 dated Mar. 14, 2014.
Summons to Attend Oral Proceedings Pursuant to Rule 115(1) EPC for European Patent App. No. 11152354.4 (Aug. 7, 2014).
Chinese Office Action for the related Chinese Patent Application No. 201110030382.9 dated Feb. 5, 2015.
Japanese Office Action for the related Japanese Patent Application No. 2010-015345 dated Jun. 24, 2014.

* cited by examiner

PORTABLE BIOLOGICAL SIGNAL MEASUREMENT/TRANSMISSION SYSTEM

BACKGROUND OF THE INVENTION

The present invention relates to a portable biological signal measurement/transmission system which includes at least one of a plurality of sensors for measuring a plurality of biological signals such as ECG, SpO2, and NIBP and which transmits biological signal information measured by the sensor to a monitoring device.

JP-T-2008-526443 discloses a related-art patient monitoring device which measures biological signals. The related-art patient monitoring device is shown in FIGS. 13 to 16. Referring to FIG. 13, the patient monitoring device 20 is defined by a housing 24 that receives input from a plurality of sensors, each forming part of physiologic sensor assemblies 28, 32 and 36, in this instance ECG, SpO2 and NIBP (non-invasive blood pressure) assemblies. The housing 24 includes a display 88 for vital sign numerics, waveforms and other patient data, as well as a user interface 92, shown in FIG. 14, that permits operation of the monitoring device 20.

Referring to FIG. 13, the display 88 is provided on a front facing side of the housing 24, as well as a plurality of adjacent actable buttons defining the user interface 92. The display 88 is a quarter (QVGA) color display, and the size of the display 88 is approximately 3.5 inches (measured diagonally). More particularly, the display 88 is an LCD having a pixel count of 240 by 320. The display 88 preferably includes a backlight (not shown) to improve readability of the display under low ambient light conditions.

As to the profile of the device 20, the size of the housing 24 is approximately 5.3 inches in height, 7.5 inches in width, and 2.0 inches in depth. In spite of the lightweight design, however, the monitoring device 20 is extremely durable and rugged in which the device is equipped to handle various loads that may be encountered in a patient-related setting. For example, the housing 24 includes a center or intermediate rubberized bladder 26 disposed between a front housing half and a rear housing half that is disposed peripherally therebetween about the device housing 24 in order to assist in cushioning the monitoring device 20 from impact or shock loads and to retain the interior of the device from dust or other contaminants. To further assist in cushioning the monitoring device 20, each of the corners of the housing 24 are curved to provide an effective contour. A battery compartment (not shown) is also formed within the housing 24, the cover of the battery compartment being essentially flush with the rear facing side 61 of the housing such the compartment does not protrude from the overall profile of the monitoring device 20. The rear facing side 61 of the housing 24 further includes a set of rubberized pads or feet 58, enabling the monitoring device 20 to be placed on a flat surface, as needed. In addition, each of the buttons included in the user interface 92 is elastomerized to aid in the overall durability and ruggedness of the monitoring device 20, the buttons being positioned so as not to overly protrude from the facing surface 84 of the housing 24 and allowing the device to maintain a relatively compact profile.

The compact profile of the device housing 24 enables the monitoring device 20 to be patient wearable. A pair of tabs 132, shown in FIG. 13, provided on opposing lateral sides of the device housing 24 enable the monitoring device 20 to be secured to a patient-wearable harness 135 or alternatively a strap 137 can be attached to the side tabs 132 permitting hand-held and portable operation of the monitoring device 20. The strap 137 can be used additionally for transport operations along with a transport belt 139 with respect to a gurney 138 or other transport apparatus. Otherwise and as noted above, the monitoring device 20 can be suitably positioned upon a table or other flat surface using the rubberized pads 58 provided on the rear facing side 61 of the device housing 24.

In addition to being compact and durable, the monitoring device 20 is extremely lightweight. The entire assemblage shown in FIG. 13 weighs approximately two pounds.

As noted above, a plurality of physiologic sensor assemblies are tethered to the housing 24, including an ECG sensor assembly 28, an SpO2 sensor assembly 32 and an NIBP sensor assembly 36, respectively, the sensor assemblies being shown in FIG. 13 only for the sake of clarity.

A brief treatment of each tethered physiologic sensor assembly 28, 32, 36 is now provided for the sake of completeness. More particularly and in brief, the SpO2 sensor assembly 32 is used to noninvasively measure oxygen saturation of arteriolar hemoglobin of a peripheral measurement site of a patient, such as the wrist, a finger, a toe, forehead, earlobe or other area. Reusable or disposable sensor probes can be used. In this instance, a finger clamp 60 is shown in FIG. 13, the clamp having a light emitter and a light detector that can be used to detect pulse/heart rate as well as blood oxygen saturation through pulse oximetry. The finger clamp 60 is tethered by means of a cable 64 extending to a pinned connector that mates with a corresponding female connecting port 44, FIG. 15, that is provided on the exterior of the device housing 24.

In brief, the ECG sensor or monitoring assembly 28 includes a lead wire assembly, in which either a three-lead or a five-lead ECG can be utilized. More particularly and by way of example, the herein pictured ECG sensor assembly 28 of FIG. 13 comprises a set of lead wires 68, each having electrodes 70 at the ends thereof to permit attachment to the body of a patient, the lead wire assembly including a harness 71 that is attached to a connection cable 72 having a connector which is matingly attachable to the connection port 40 of the device housing 24. The ECG sensor assembly 28 is further utilized herein with respect to a respiration channel of the monitoring device 20 in order to determine the rate or absence (apnea) of respiration effort through the determination of ac impedance between selected terminals of ECG electrodes 70, thereby determining the respiration rate of a patient using impedance pneumography based upon movements of the chest wall using a designated reference lead wire. Heart rate is detected for the device 20 using the ECG sensor assembly 28.

The ECG sensor assembly 32 creates a waveform (ECG vector) for each lead and further includes a QRS detector that can be adjusted depending upon the patient mode selected. The ECG sensor assembly 28 is further configured to determine heart/pulse rate, if selected, as well as mark pacer spikes in the resulting ECG waveforms byway of a pacer detection circuit. The ECG sensor assembly 28 further includes selectable notch filters of 50 Hz and 100 Hz, 60 Hz and 120 Hz, respectively.

In brief, the NIBP sensor assembly 36 indirectly measures arterial pressure using an inflatable cuff or sleeve 76, which is attached to the limb (arm or leg) of a patient (not shown). The remaining end of a connected hose 80 includes an attachment end that can be screwed into a fitted air connector fitting 48 that is provided on the top facing side of the housing 24. The air connector fitting 48 is connected to a pump (not shown) disposed within the monitoring device housing 24 in order to selectively inflate and deflate the cuff 76 to a specified pressure, depending on the type of patient, using the oscillometric method. Pressure changes are detected by means of circuitry in order to determine systolic, diastolic and mean arterial pressure (MAP). The NIBP sensor assembly 36 is capable of performing manual, automatic and a turbo mode of operation. The assembly 36 can also be equipped, when ECG is also being monitored, with a motion artifact filter if ECG is also being monitored. The filter employs a software algorithm that can be used to automatically synchronize the process of NIBP measurement to the occurrences of the R-wave of the ECG waveform, thereby increasing accuracy in cases of extreme artifact and diminished pulses. An example of a suitable NIBP artifact filter is described in U.S. Pat. No. 6,405,076. Examples of NIBP and ECG sensor assemblies useful for incorporation into the monitoring device 20 are manufactured by Welch Allyn Inc., of Skaneateles Falls, N.Y., among others. With regard to each, the form of sensor assembly can be varied depending on the type of patient, (i.e., adult, pediatric, neonatal) by selective attachment to the connection ports 40, 48 that are provided on the monitoring device 20. Each of the foregoing sensor assemblies further includes electrosurgery interference suppression. As noted, pulse rate can be detected from either the SpO2 or the NIBP channels of the monitoring device 20.

It is contemplated, however, that other means for connecting the above noted sensor assemblies 28, 32 to the monitoring device 20 other than through the connection ports 40, 44, including wireless means, such as for example, IR, optical, RF, and other nontethered connections could also be employed. It should be further noted that the number of types of physiologic sensor assemblies used with the device 20 can be varied.

Referring to FIGS. 13 and 16, each of the above physiologic sensor assemblies 28, 32, 36 are internally connected electrically to a CPU 174 that is contained within the housing 24 of the monitoring device 20. Signal processing for each of the physiologic sensor assemblies 28, 32, 36 is performed internally through resident processing circuitry, for example, the SpO2 sensor assembly 32 utilizes the Nellcor Puritan MP506 architecture while the NIBP sensor assembly 36 is based upon a design, such as those used in the Micropaq and Propaq vital signs monitors, including, for example, an NIBP Module, Part 007-0090-01, manufactured and sold by Welch Allyn, Inc. Though not shown in FIG. 16, the resident circuitry for each of the sensor assemblies 28, 32, 36 are all integrated into a single logic board in which the ECG and respiration parameters utilize a common processor, such as a Motorola MPC 823 processor of the CPU 174. Despite being integrated into a single logic board, the remaining physiologic parameters (SpO2 and NIBP) are implemented in a more modular fashion, and utilize their own processors.

Still referring to the schematic diagram of FIG. 16, the contained battery pack 170 is interconnected to the CPU 174, the latter including a microprocessor, memory, and resident circuitry, in which each are connected to the tethered sensor assemblies 28, 32, 36 in order to enable processing storage and selective display of the signals provided therefrom as well as perform power conversion between the charging circuit of an optional charging cradle 140 and the contained battery pack, including circuitry to prevent overcharging of the contained battery pack 170 (i.e., 12 volts to 5 volts). The CPU 174 includes available volatile and non-volatile storage for patient data, in the form of Flash memory and SRAM, though other form as are also possible, the CPU 174 being further connected to the display 88. As noted above, the CPU 174 is presented on a single logic board along with the processors for the physiologic sensor assemblies 28, 32, 36. The CPU 174 is intended to handle device-specific aspects, such as alarm limits, display generation, and enabling and disabling of certain features, in which the physiologic sensor assemblies 28, 32, 36 predominantly only relate data for use by the CPU 174. It should be noted that portions of the processing function, for example, the ECG processing algorithms, can also reside in CPU 174, though this can be varied appropriately depending, for example, on the extent of processing power required or packaging concerns. The CPU 174, predominantly controls the operation of the device 20, including patient modes, pressures, voltages and the like, as a factory default setting, or either through the user interface 92, a remote monitoring station 184, shown in FIG. 16, and/or a connected PC 192, shown in FIG. 16.

In addition to the preceding, the monitoring device 20 as schematically represented in FIG. 16 further optionally includes a wireless radio card/transceiver 180, enabling bi-directional wireless communication with at least one remote monitoring station 184, such as, for example, the Acuity Monitoring Station manufactured and sold by Welch Allyn Inc., using the radio card as inserted in an internal PCMCIA expansion slot (not shown). The radio card 180 is an IEEE802.11 compliant radio card that connects to an antenna 182 that is also disposed within the housing 24 of the monitoring device 20 for transmission over a 2.4 GHz frequency hopping spread spectrum (FHSS) wireless local area network (WLAN) using access points 186. Additional details relating to an exemplary wireless interconnection, including networking therewith, is described in U.S. Pat. No. 6,544,174.

As most clearly shown in FIG. 14, a lower or bottom facing surface 120 of the device housing 24 includes a latching member 124, shown in FIG. 14, as well as an electrical port 128, shown in FIG. 14, each of which are used in conjunction with an optional charging cradle 140. As previously noted, the battery pack 170, only shown schematically in FIG. 16, is contained in the rear of the device housing 24 within a rear compartment (not shown). The battery pack 170 provides portable power for the monitoring device 20 in which the battery life is dependent upon certain operational modes of the device. The battery pack 170 is rechargeable by means of charging circuitry contained within the optional charging cradle 140. The battery pack 170 includes at least one rechargeable lithium-ion battery, such as those manufactured by Sanyo Corporation. In this instance, the battery pack 170 includes two rechargeable batteries. The monitoring device 20 is capable of operation in a stand-alone mode using the contained battery 170 as a power source, the battery having an average runtime of up to approximately 24 hours, depending on the usage of the device.

In the related-art patient monitoring device disclosed in JP-T-2008-526443, the ECG, SpO2, and NIBP sensor assemblies are individually disposed, the plurality of sensor assemblies are connected to the patient monitoring device through the connector, and all signal processing (for example, signal amplification, A/D conversion, and filtering) of biological signal information measured by the ECG, SpO2, and NIBP sensor assemblies are conducted by the CPU in the patient monitoring device.

Therefore, the related-art patient monitoring device must be provided with a function to process biological signal information measured by the ECG, SpO2, and NIBP sensor assemblies. This limitation causes the following disadvantages; the process burden of the CPU mounted on the patient monitoring device is large, a dedicated device is required for various combinations of parameters, and the patient monitoring device is expensive and bulky so that the patient cannot move around while carrying the patient monitoring device. Furthermore, the measurable parameters are fixed by the design of the patient monitoring device. In the case of a related-art patient monitoring device such as described above, for example, when only ECG monitoring is applied to a non-severe patient, a hospital has to use an over-specified device for this patient which can measure all of the ECG, SpO2, and NIBP parameters. Thereby, it causes a problem in efficiency of apparatus management and operation.

SUMMARY

It is therefore an aspect of the invention to provide a biological signal measurement/transmission system, which is economical and portable and in which a biological signal processing unit including a signal processing portion that performs processing (for example, signal amplification, A/D conversion, and filtering) on measurement data such as ECG, SpO2, and NIBP data, is configured so as to be separable from a body unit, whereby the burden of signal processing in the body unit is reduced so that a small data processing terminal or the like having a high versatility can be employed as the body unit, and further in which a signal processing unit corresponding to a single or plurality of sensor devices can be selectively connected to the body unit depending on the use required by the user, whereby it is possible to realize a less wasteful system which corresponds to the use.

In order to achieve the object, according to the invention, there is provided a portable biological signal measurement/transmission system comprising: a body unit; and at least one biological signal processing unit detachably connected to the body unit, and including a signal processor which processes a biological signal, the biological signal processing unit including a first transmitter which transmits the biological signal to the body unit when the biological signal processing unit is connected to the body unit.

The biological signal processing unit may include a connector to which a measuring sensor which measures the biological signal is to be connected.

The signal processor may perform at least one of a signal amplifying process, a filtering process, and an A/D converting process on the biological signal.

The body unit may include a second transmitter which wirelessly transmits the biological signal, which is received from the biological signal processing unit, to a biological signal remote monitoring device or a patient monitoring device.

The body unit may include: a battery portion; a storage portion which stores the biological signal, which is received from the biological signal processing unit; an analyzing portion which analyzes the biological signal; a displaying portion which displays the biological signal and the processed data; and an alarm generating portion which generates an alarm related to the biological signal.

The body unit may be connected to a cradle unit that charges a battery portion of the body unit, and when the body unit is connected to the cradle unit, the biological signal is transmitted to a biological signal remote monitoring device or a patient monitoring device through the cradle unit.

The cradle unit may include a body temperature probe which performs a spot or continuous measurement of a body temperature.

The biological signal may include at least one of ECG data, SpO2 data, and NIBP data.

In order to achieve the object, according to the invention, there is also provided a biological signal processing unit comprising: a signal processor which processes a biological signal; an attaching unit which attaches the biological signal processing unit to a patient; and a nurse call switch, wherein the biological signal processing unit is detachably connected to a body unit.

The attaching unit may be a clip which is attachable to clothes of the patient.

The biological signal may include at least one of ECG data, SpO2 data, and NIBP data.

DETAILED DESCRIPTION OF EMBODIMENTS

Figure 1:
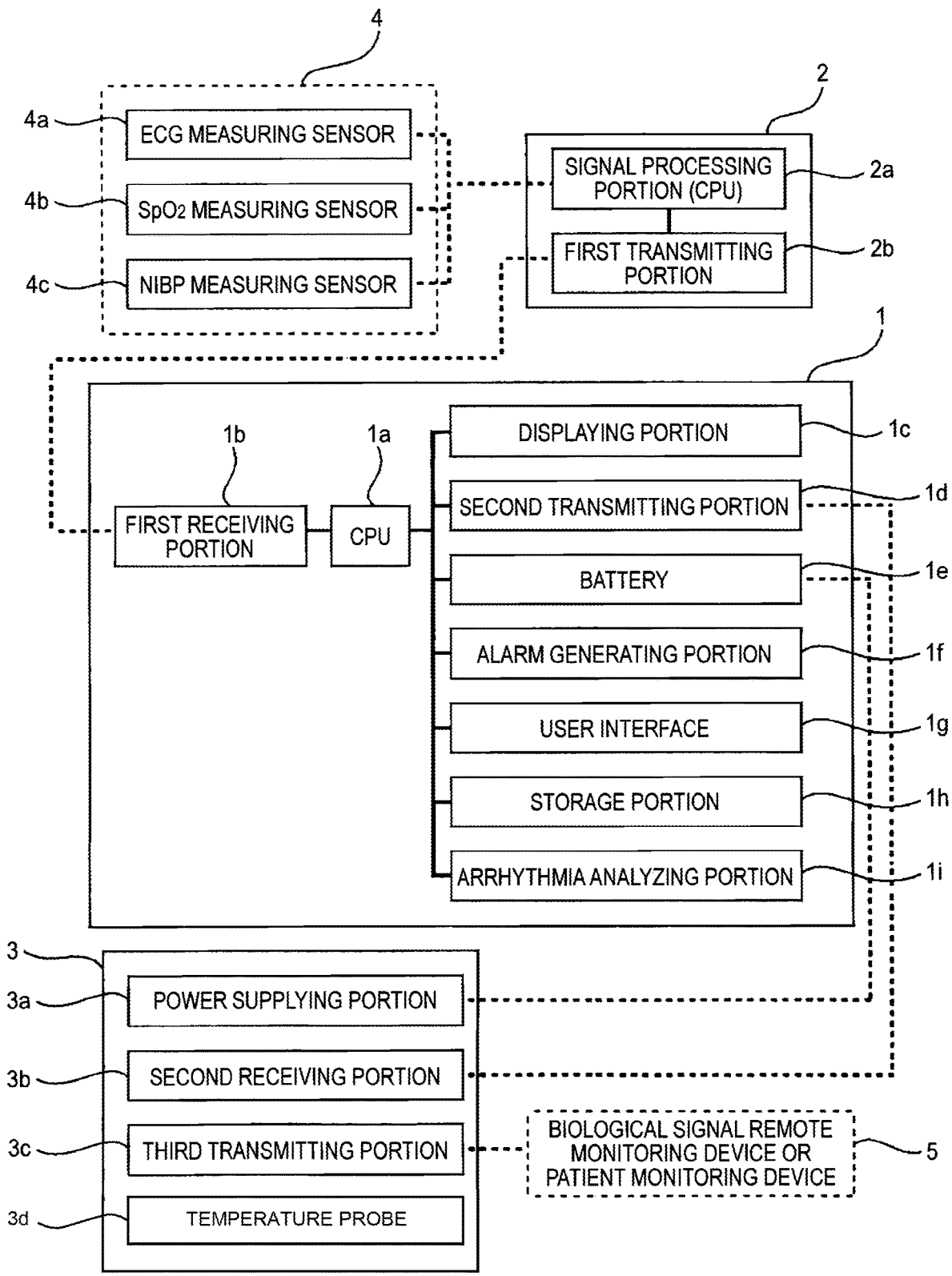
FIG. 1 is a block diagram showing the whole configuration of a portable biological signal measurement/transmission system of the invention.

The whole configuration of the portable biological signal measurement/transmission system of the invention will be described with reference to FIG. 1. FIG. 1 is a block diagram showing the whole configuration of the portable biological signal measurement/transmission system of the invention. In FIG. 1, the reference numeral 1 denotes a body unit which includes a processing unit (CPU) 1a, a first receiving portion 1b, a displaying portion 1c, a second transmitting portion 1d, a battery 1e, an alarm generating portion 1f, a user interface 1g, a storage portion 1h, and an arrhythmia analyzing portion 1i.

The reference numeral 2 denotes a biological signal processing unit which includes a signal processing portion (CPU) 2a and a first transmitting portion 2b. The reference numeral 3 denotes a cradle unit which charges the battery of the body unit 1. The cradle unit 3 includes a power supplying portion 3a, a second receiving portion 3b, and a third transmitting portion 3 and a temperature probe 3d. The reference numeral 4 denotes a biological signal measuring sensor which includes an ECG (electrocardiogram) measuring sensor 4a, an SpO2 measuring sensor 4b, an NIBP measuring sensor 4c, and other sensors (not shown). The reference numeral 5 denotes a biological signal remote monitoring device or patient monitoring device which is placed in a nurse's station or the like.

Preferably, when connected to the cradle unit 3, the body unit 1 may transmit a biological signal received from the biological signal processing unit 2, by means of wired transmission to the biological signal remote monitoring device 5 through the third transmitting portion 3c of the cradle unit 3, and, when not connected to the cradle unit 3, the body unit 1 may transmit the biological signal by means of wireless transmission to the biological signal remote monitoring device 5 through the second transmitting portion 1d in the body unit.

Furthermore, the body unit 1 can store the biological signal received from the biological signal processing unit 2, in the storage portion 1h, and the stored data may be preferably referenced on the displaying portion 1c. In the case where a transmission failure occurs and the biological signal cannot be transmitted to the biological signal remote monitoring device 5, particularly, the biological signal is stored in the storage portion 1h, and hence there is an advantage that data can be prevented from being lost.

Figure 2:
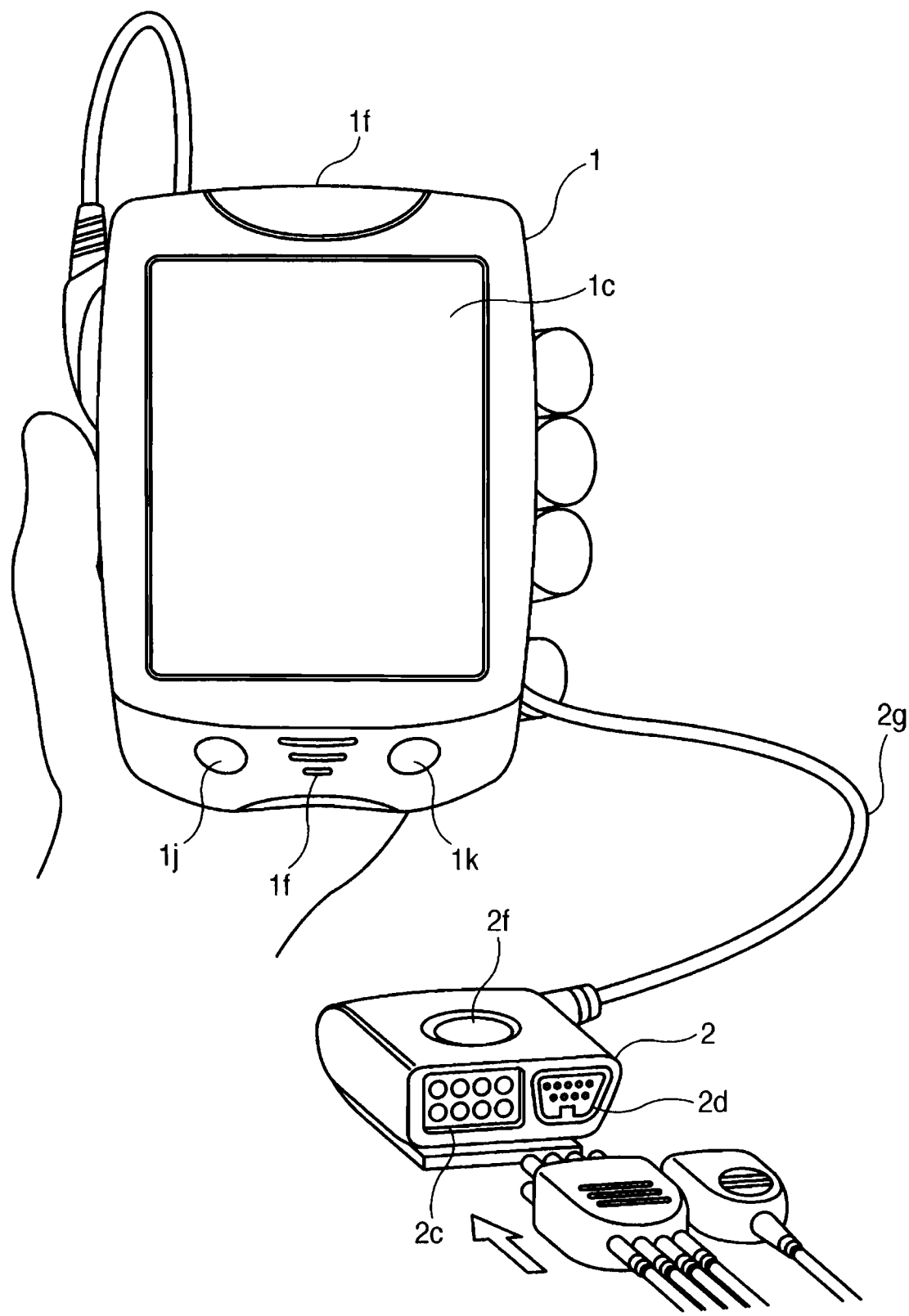
FIG. 2 is a perspective view showing a body unit and a biological signal processing unit in a first embodiment of the invention.

Next, the components of the portable biological signal measurement/transmission system of the invention will be described with reference to FIGS. 2 to 10. FIG. 2 is a perspective view showing in detail the body unit 1 and the biological signal processing unit 2 in a first embodiment of the invention. In FIG. 2, 1 denotes the body unit, and 1c denotes the displaying portion which uses a color LED, and which is preferably configured as a touch panel. The reference numeral 1f in the upper side denotes an alarm indicator which is configured by an LCD, and which emits color light that is different depending on the kind of the alarm, and 1f in the lower side denotes an alarm speaker which notifies a sound alarm that is different depending on the kind of the alarm. The reference numeral 1j denotes a record key, and 1k denotes an alarm cancel key.

In FIG. 2, 2 denotes the biological signal processing unit, 2f denotes a nurse call key (nurse call switch), 2c denotes a connector for connection with the ECG measuring sensor, 2d denotes a connector for connection with the SpO2 measuring sensor, and 2g denotes a connection cable for connection with the body unit. In the biological signal processing unit 2 in the figure, the measurement objects are the ECG and the SpO2.

Figure 3:
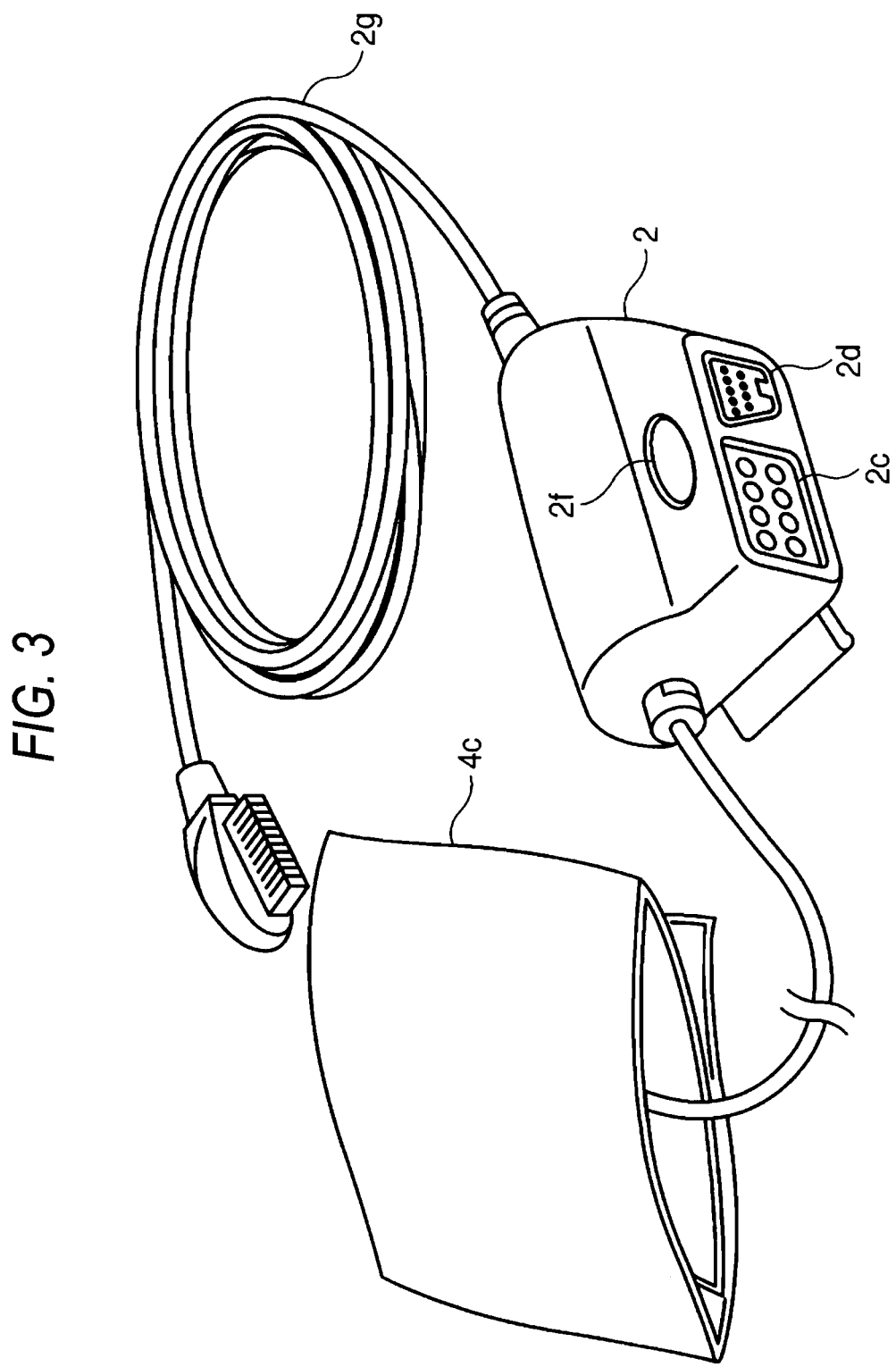
FIG. 3 is a view of an example in which an NIBP measuring unit is fixedly connected to a biological signal processing unit.

Next, a modification of the biological signal processing unit 2 of FIG. 2 will be described with reference to FIG. 3. The biological signal processing unit 2 of FIG. 3 shows an example in which the NIBP measuring unit 4c is already fixedly connected to the biological signal processing unit 2, and, in addition to a measurement of NIBP, measurements of ECG and SpO2 can be selected as required.

Figure 4:
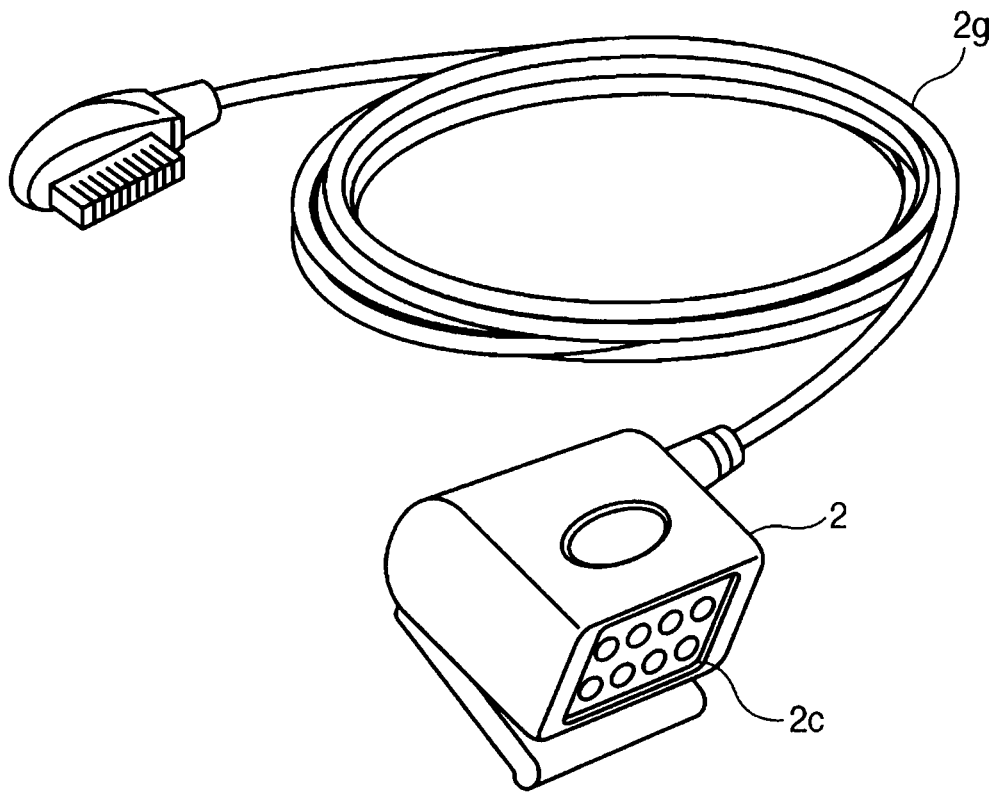
FIG. 4 is a view of an example in which a biological signal processing unit is specialized to a measurement of ECG.

Next, another modification of the biological signal processing unit 2 of FIG. 2 will be described with reference to FIG. 4. The biological signal processing unit 2 of FIG. 4 is specialized to the measurement of ECG, and used in the case where only the measurement of ECG is required. Although FIG. 4 shows the case where the biological signal processing unit 2 can be used only in the measurement of ECG, it is obvious that the biological signal processing unit 2 may be specialized to another measurement object or the measurement of SpO2 or NIBP.

Figure 5:
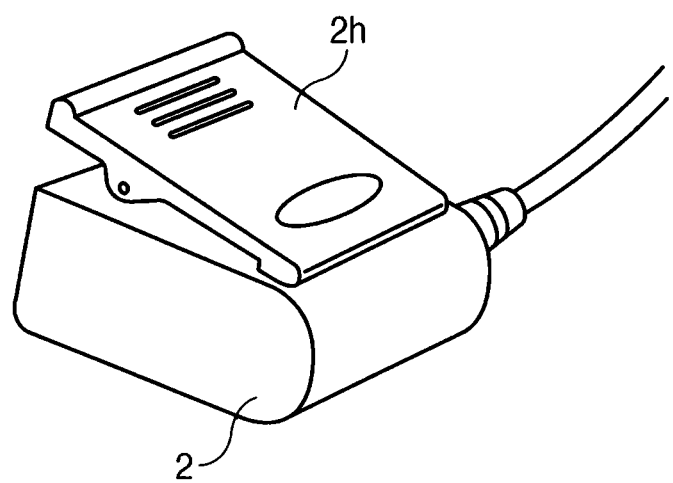
FIG. 5 is a view showing the rear side of the biological signal processing unit.

Next, a configuration example of the biological signal processing unit 2 of FIG. 2 will be described with reference to FIG. 5. FIG. 5 shows the rear side of the biological signal processing unit 2. The configuration of the rear side is common to the biological signal processing units 2 of FIGS. 2 to 4. As shown in the figure, a clip 2h which functions as an attaching unit for attaching the biological signal processing unit 2 to clothes or the like of the patient is disposed in the rear side of the biological signal processing unit 2. As the attaching unit, any unit other than a clip may be used as far as the unit can fix the biological signal processing unit 2 to clothes or the like of the patient.

In a related-art patient monitoring device, a cable which extends from a sensor assembly is connected directly to a body unit. When the sensor assembly is to be attached to the patient, therefore, it is difficult to lay the cable, and the difficulty may cause the so-called spaghetti syndrome. In the invention, by contrast, a cable which extends from a sensor assembly is not connected directly to the body unit 1, but once connected to the biological signal processing unit 2 which can be placed in the vicinity of the body of the patient. Therefore, the cable can be shortened, and, when the sensor assembly is to be attached to the patient, the cable can be easily laid. Moreover, the clip 2h is disposed in the biological signal processing unit 2, and cables and the like can be housed in the vicinity of the body of the patient. Therefore, it can be said that cable laying is further facilitated.

In the invention, the functions, which, in a related-art patient monitoring device, are concentrated into a so-called monitoring device, are dispersed between the body unit 1 and the biological signal processing unit 2, and hence the body unit 1 can be miniaturized and lightened. When the patient is to move, therefore, the body unit can be easily carried. Moreover, a larger battery can be mounted, and long term monitoring is enabled.

Figure 6:
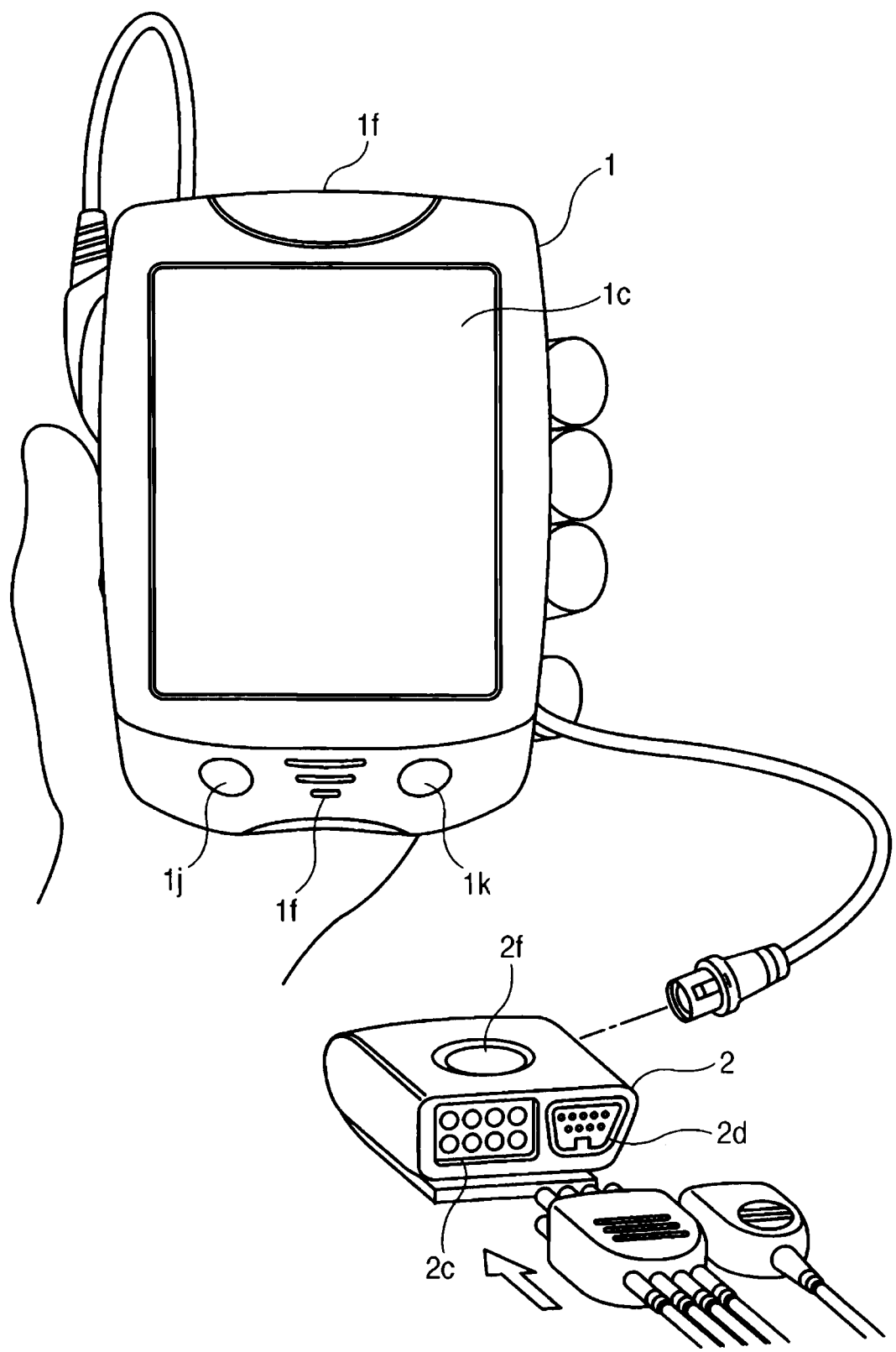
FIG. 6 is a perspective view showing a body unit and a biological signal processing unit in a second embodiment of the invention.

FIG. 6 is a perspective view showing in detail a body unit and a biological signal processing unit in a second embodiment of the invention. In FIG. 6, 1 denotes the body unit, and 1c denotes a displaying portion which uses a color LED, and which is preferably configured as a touch panel. The reference numeral 1f in the upper side denotes an alarm indicator which is configured by an LCD, and which emits color light that is different depending on the kind of the alarm, and 1f in the lower side denotes an alarm speaker which notifies a sound alarm that is different depending on the kind of the alarm. The reference numeral 1j denotes a record key, and 1k denotes an alarm cancel key.

In FIG. 6, 2 denotes the biological signal processing unit, 2f denotes a nurse call key (nurse call switch), 2c denotes a connector for connection with the ECG measuring sensor, 2d denotes a connector for connection with the SpO2 measuring sensor, and 2g denotes a connection cable for connection with the body unit 1. In the biological signal processing unit 2 in the figure, the measurement objects are the ECG and the SpO2. The biological signal processing unit 2 of FIG. 6 is different from that of FIG. 2 in that the connection cable 2g for connection with the body unit 1 is configured so as to be separable also from the biological signal processing unit 2. When this configuration is employed, the biological signal processing unit 2 can be used while its kind is selected depending on the patient. Therefore, wasteful functionality can be reduced.

Figure 7:
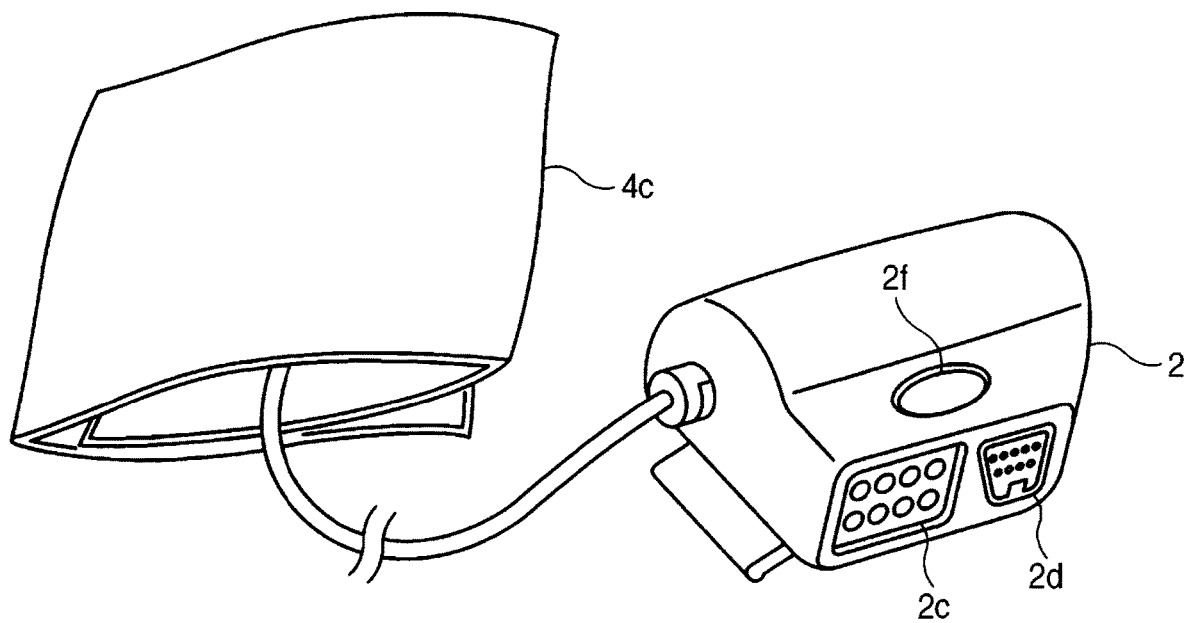
FIG. 7 is a view of an example in which an NIBP measuring unit is fixedly connected to a biological signal processing unit.

Next, a modification of the biological signal processing unit 2 of FIG. 3 will be described with reference to FIG. 7. The biological signal processing unit 2 of FIG. 7 shows an example in which the NIBP measuring unit 4c is already fixedly connected to the biological signal processing unit 2, and, in addition to a measurement of NIBP, measurements of ECG and SpO2 can be selected as required. The biological signal processing unit 2 of FIG. 7 is different from that of FIG. 3 in that the connection cable 2g for connection with the body unit is configured so as to be separable also from the biological signal processing unit 2. When this configuration is employed, the biological signal processing unit 2 can be used while its kind is selected depending on the patient. Therefore, wasteful functionality can be reduced.

Figure 8:
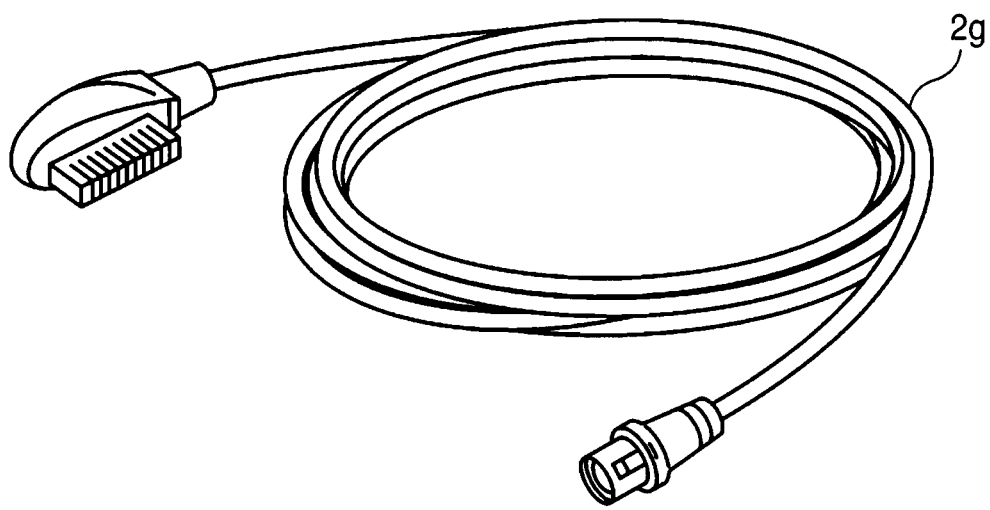
FIG. 8 is a view of a connection cable through which a body unit and a biological signal processing unit are connected to each other.

Next, the connection cable 2g which is used in the biological signal processing units 2 of FIGS. 6 and 7 will be described with reference to FIG. 8. The connection cable of FIG. 8 connects between the body unit 1 and the biological signal processing unit 2, and can be applied to any kind of biological signal processing unit.

Figure 9:
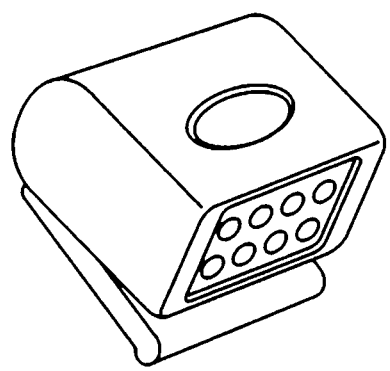
FIG. 9 is a view of an example in which a biological signal processing unit is specialized to a measurement of ECG.

Next, a modification of the biological signal processing unit 2 of FIG. 4 will be described with reference to FIG. 9. The biological signal processing unit 2 of FIG. 9 is specialized to the measurement of ECG, and used in the case where only the measurement of ECG is required. The biological signal processing unit 2 of FIG. 9 is different from that of FIG. 4 in that the connection cable 2g for connection with the body unit 1 is configured so as to be separable also from the biological signal processing unit 2. When this configuration is employed, the biological signal processing unit 2 can be used while its kind is selected depending on the patient. Therefore, wasteful functionality can be reduced. Although FIG. 9 shows the case where the biological signal processing unit 2 is specialized to the measurement of ECG, it is obvious that the biological signal processing unit 2 may be specialized to the measurement of SpO2 or NIBP. The measurement objects of the biological signal processing unit 2 are not limited to ECG, SpO2, and NIBP, and the biological signal processing unit 2 may be configured so as to be expandable to measure other measurement objects such as Temp (body temperature) and CO2 (concentration of expiratory carbon dioxide).

Figure 10:
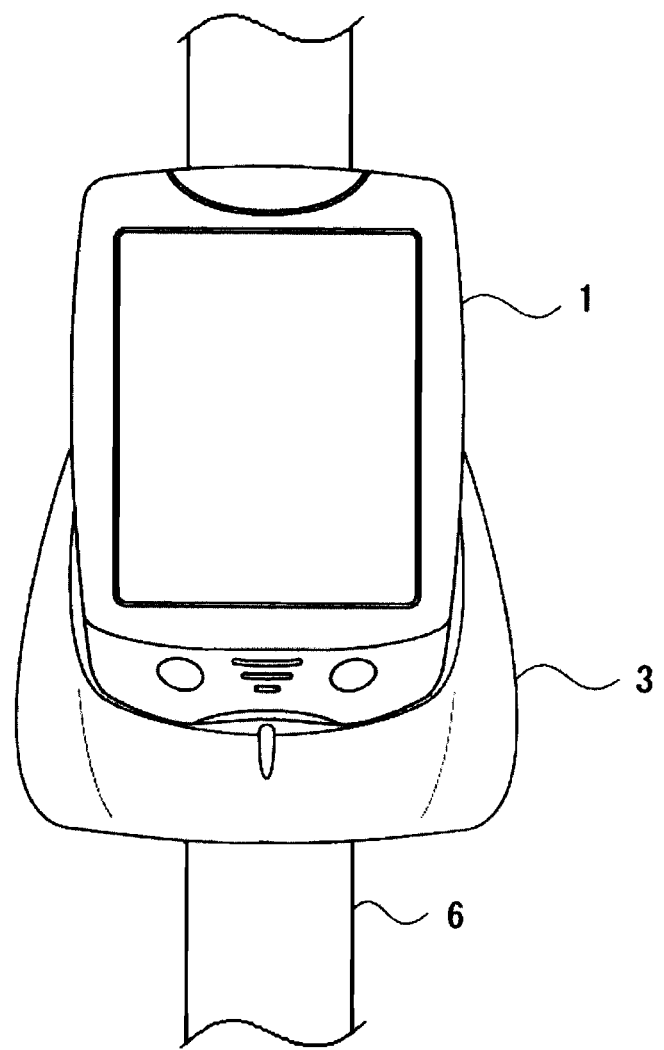
FIG. 10 is a view showing a state where the body unit is connected to a cradle unit.

FIG. 10 is a view showing a state where the body unit 1 is connected to the cradle unit 3. The cradle unit 3 is fixed to an intravenous pole 6. In this state, the battery 1e of the body unit 1 is charged by the power supplying portion 3a of the cradle unit 3. Measurement data are transmitted from the second transmitting portion 1d of the body unit 1 to the biological signal remote monitoring device 5 through the second receiving portion 3b and third transmitting portion 3c of the cradle unit 3.

Figure 11:
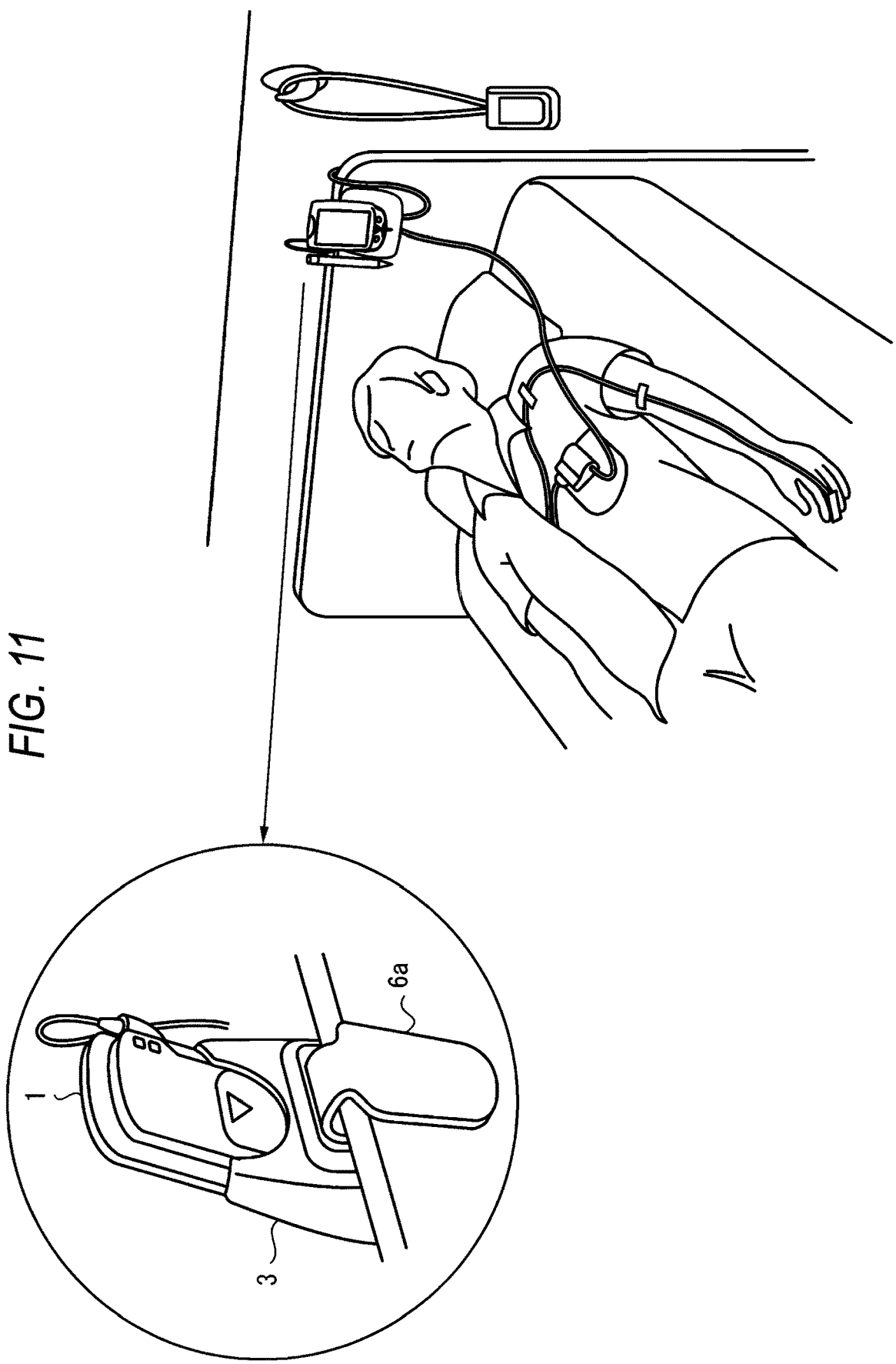
FIG. 11 is a view showing the body unit which is fixed to a bed of the patient in the state where the body unit is connected to the cradle unit.
Figure 12:
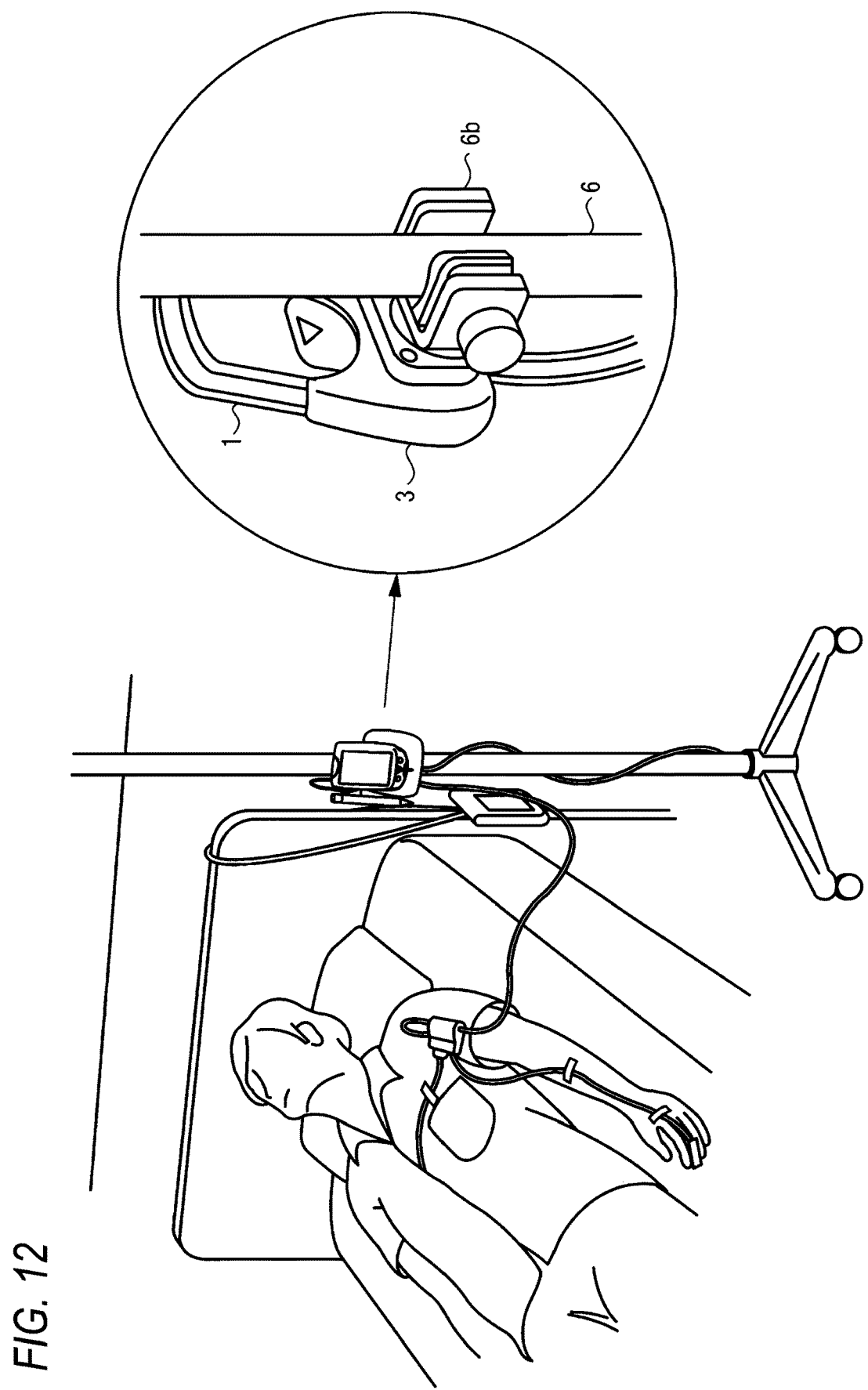
FIG. 12 is a view showing the body unit which is fixed to an intravenous pole near a bed of the patient in the state where the body unit is connected to the cradle unit.
Figure 13:
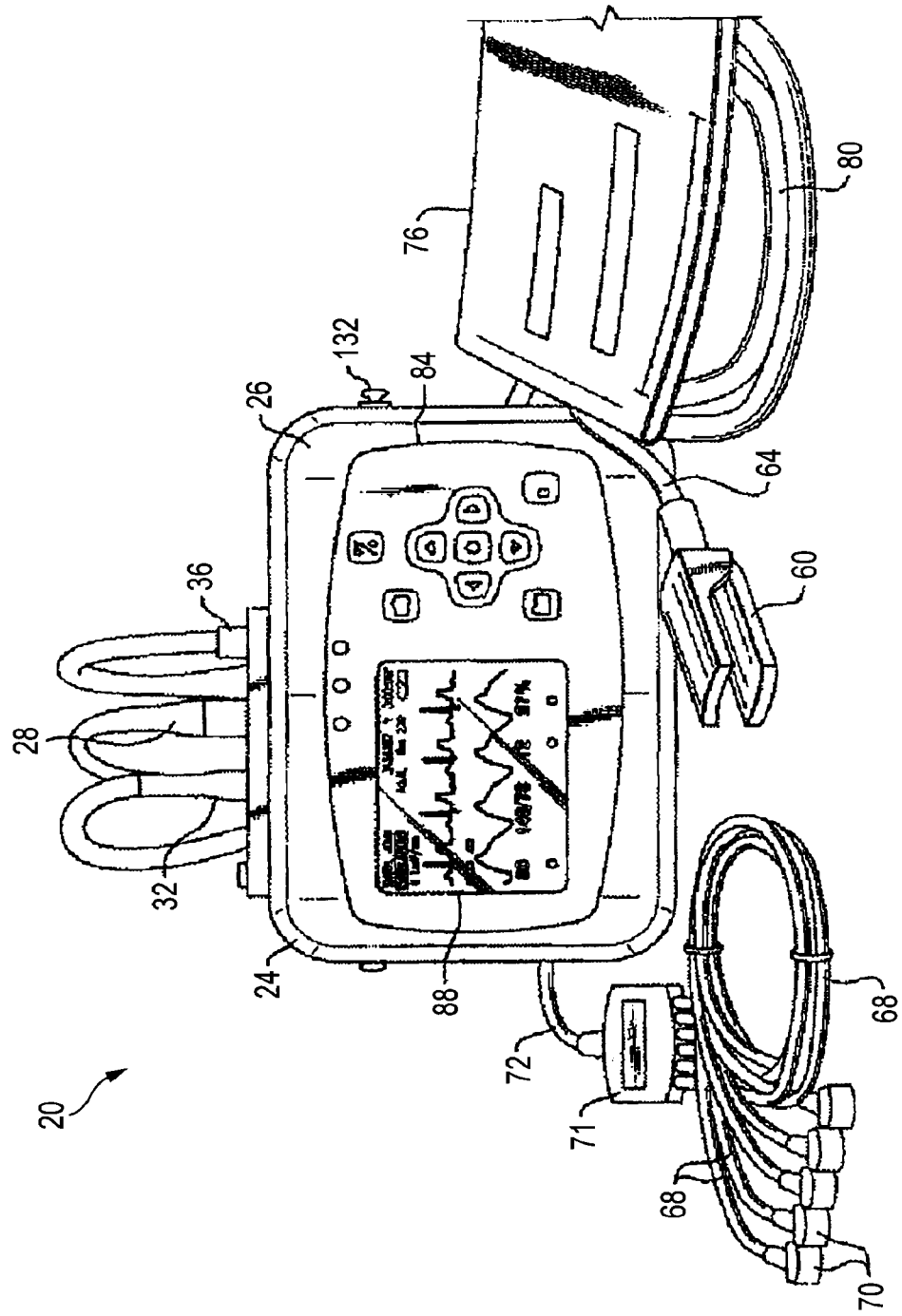
FIG. 13 is a front view of a related-art patient monitoring device.
Figure 14:
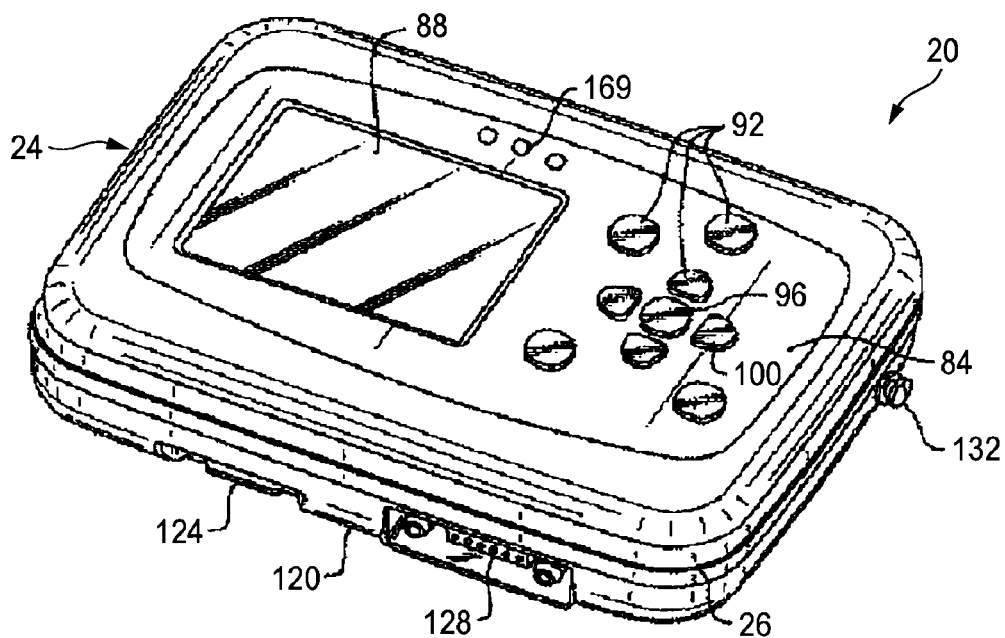
FIG. 14 is a front perspective view of the related-art patient monitoring device of FIG. 13.
Figure 15:
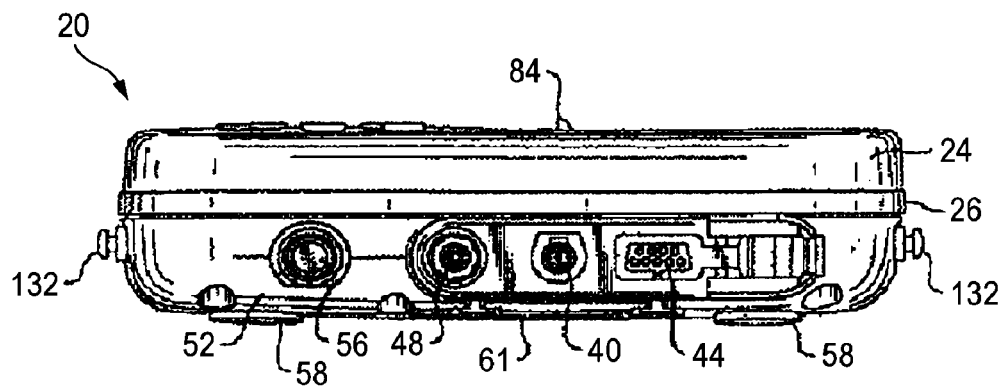
FIG. 15 is a vertical front view of the related-art patient monitoring device of FIGS. 13 and 14.
Figure 16:
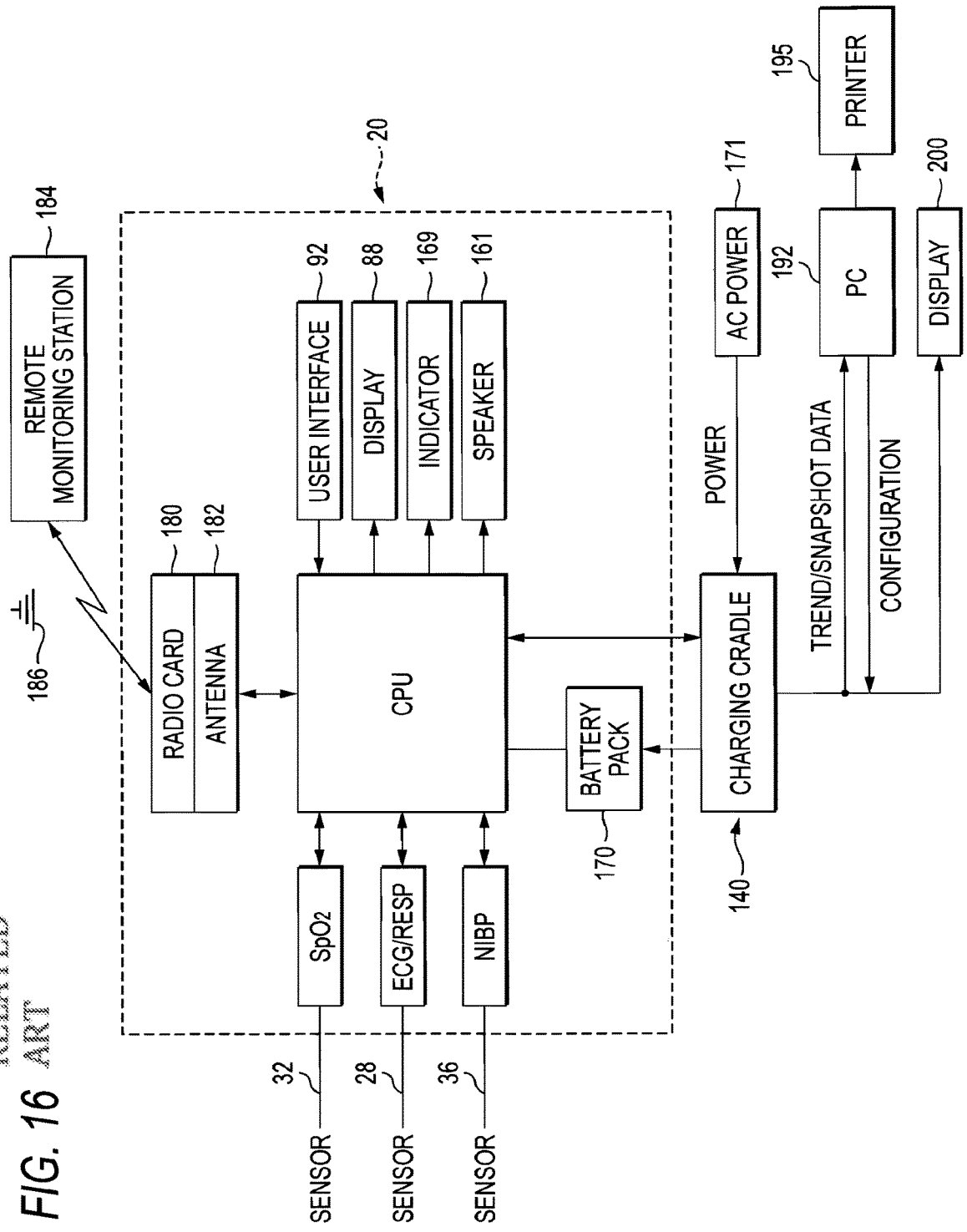
FIG. 16 is a schematic block diagram of a patient monitoring system including the related-art patient monitoring device of FIGS. 13 to 15 and a charging cradle.

FIGS. 11 and 12 show examples in which the body unit 1 is fixed in the state where the body unit 1 is connected to the cradle unit 3. In FIG. 11, the body unit 1 is fixed to a part of the head side of a bed of the patient by a fixing device 6a, and, in FIG. 12, the body unit 1 is fixed to an intravenous pole 6 for the patient by a mounting device 6b. Preferably, the cradle unit 3 has a structure which enables the structure to be disposed in the vicinity of the patient. Alternatively, the cradle unit 3 may have a structure which includes a body temperature measuring probe 3d that allows a nurse to perform a spot or continuous measurement of the body temperature on the patient. Data which are related to the body temperature, and which are measure by the probe 3d may be displayed on the displaying portion 1c, and, transmitted to the biological signal remote monitoring device or the patient monitoring device 5 through the cradle unit 3.

As in the biological signal processing unit 2 shown in FIGS. 2 to 4 (or FIGS. 6 to 8), the system of the invention is configured by one of the group of a plurality of kinds of biological signal units, and the body unit 1, or the invention is a so-called combination invention. The configuration which is common to all the embodiments, and which is important is that the group of biological signal units has a common interface, and each of the biological signal units 2 are attachable and detachable to and from the body unit 1. According to the configuration, simply by replacing the biological signal processing unit 2 with another one, the user can select the parameter to be measured. Although, in the embodiments, the connection example in which the biological signal processing unit 2 is connected with the wire to the body unit 1 has been described, the invention is not limited to wired-connection.

As described above, unlike the related art, it is not required to respectively prepare patient monitoring devices for parameters to be measured. It is simply necessary that the common body unit is prepared, and an adequate one of the biological signal processing units is connected to the body unit depending on the use. Therefore, not only the cost, but also the expandability, the maintainability, and the efficiency of the apparatus management can be remarkably improved.

According to an aspect of the invention, the biological signal processing unit which processes measurement data such as ECG, SpO2, and NIBP data, and which corresponds to a single or plurality of sensor devices is separable from the body unit constituting the portable biological signal measurement/transmission system. Therefore, the user can select a measuring sensor in accordance with the necessity in measurement of a biological signal of the patient. Consequently, the cost can be reduced, the maintainability can be improved, and the efficiency of the apparatus management can be enhanced.

Since a part of functionality of a related-art patient monitoring device is separated to the biological signal processing unit, furthermore, a small data processing terminal or the like having a high versatility can be used as the body unit, so that the cost of the body unit can be reduced and the patient can move around while carrying the body unit.

What is claimed is:

1. A portable biological signal measurement and transmission system comprising:
   at least two sensors configured to measure biological signals, wherein the biological signals include electrocardiographic (ECG) data, blood oxygen saturation (SpO2) data, and non-invasive blood pressure (NIBP) data;
   a body unit; and
   a biological signal processing unit being attachable to and detachable from the body unit and being connected to the at least two sensors,
   the biological signal processing unit including:
      a connection cable detachably connected to the body unit;

a signal processor which performs a signal amplifying process on a biological signal; and
a first transmitter which transmits the biological signal to the body unit when the biological signal processing unit is connected to the body unit through the connection cable, and
the body unit including:
a battery portion;
a storage portion which stores the biological signal, which is received from the biological signal processing unit;
an analyzing portion which analyzes the biological signal;
a displaying portion which displays the biological signal; and
a second transmitter which wirelessly transmits the biological signal.

2. The system according to claim 1, wherein the biological signal processing unit includes a connector configured to connect one of the at least two sensors to the biological signal processing unit.

3. The system according to claim 1, wherein the signal processor performs at least one of a filtering process and an analog-to-digital (A/D) converting process on the biological signal.

4. The system according to claim 1, wherein the second transmitter wirelessly transmits the biological signal, which is received from the biological signal processing unit, to a biological signal remote monitoring device or a patient monitoring device.

5. The system according to claim 1, wherein the body unit includes an alarm generating portion which generates an alarm related to the biological signal.

6. The system according to claim 1, wherein the body unit is connected to a cradle unit that charges a battery portion of the body unit, and when the body unit is connected to the cradle unit, the second transmitter transmits the biological signal to a biological signal remote monitoring device or a patient monitoring device through the cradle unit.

7. The system according to claim 6, wherein the cradle unit includes a body temperature probe which performs a spot or continuous measurement of a body temperature.

8. The system according to claim 1, wherein the biological signal processing unit includes a plurality of biological signal processing units which includes signal processors which perform a signal amplifying process on different biological signals, respectively, and one of the plurality of biological signal processing units is selectively connected to the body unit through the connection cable.

9. The system according to claim 1, wherein the connection cable is detachable from the biological signal processing unit.

10. The system according to claim 1, wherein the biological signal processing unit is provided with a first measuring sensor which measures the biological signal, and a second measuring sensor which measures another biological signal.

11. A biological signal processing unit being attachable to and detachable from a body unit and being connected to at least two sensors for measuring biological signals, wherein the biological signals include electrocardiographic (ECG) data, blood oxygen saturation SpO2 data, and non-invasive blood pressure (NIBP) data, the body unit including: a battery portion; a storage portion which stores a biological signal, which is received from the biological signal processing unit; an analyzing portion which analyzes the biological signal; a displaying portion which displays the biological signal; and a second transmitter which wirelessly transmits the biological signal, the biological signal processing unit comprising:
a signal processor which performs a signal amplifying process on a first biological signal; and
a connection cable detachably connected to the body unit to which another biological signal processing unit for performing a signal amplifying process on a biological signal different from the first biological signal can be connected.

12. The biological signal processing unit according to claim 11, further comprising an attaching unit configured to be attached to a patient.

13. The biological signal processing unit according to claim 12, wherein the attaching unit is a clip which is attachable to clothes of the patient.

14. The biological signal processing unit according to claim 11, further comprising a nurse call switch.

15. The biological signal processing unit according to claim 11, further comprising a first transmitter which transmits the first biological signal to the body unit when the biological signal processing unit is connected to the body unit through the connection cable.

16. The biological signal processing unit according to claim 11, wherein the connection cable is detachable from the biological signal processing unit.

17. The biological signal processing unit according to claim 11, further comprising a first connector to which a first measuring sensor which measures the first biological signal is to be connected.

18. The biological signal processing unit according to claim 17, further comprising a second connector to which a second measuring sensor which measures a second biological signal that is different from the first biological signal is to be connected.

19. A portable biological signal measurement and transmission system comprising:
a pulse oximetry sensor;
a biological signal processor connected to the pulse oximetry sensor, the biological signal processor being configured to amplify a signal detected by the pulse oximetry sensor; and
a portable device detachably connected to the biological signal processor via a connection cable,
the portable device comprising:
a battery;
a processor configured to analyze a biological signal received from the biological signal processor via the connection cable;
a storage portion that stores the biological signal and/or the analyzed biological signal; and
a display that displays the analyzed biological signal.

20. A biological signal processing unit, which is attachable to and detachable from a body unit, and to which at least one sensor for measuring a biological signal of a patient is connectable, the biological signal processing unit comprising:
a first cable connected to the sensor;
a signal processor configured to receive the biological signal measured by the sensor through the first cable, and configured to perform a signal amplifying process on the received biological signal;
a second cable detachably connected to the body unit; and
a transmitter configured to transmit the biological signal processed by the signal processor through the second cable when the biological signal processing unit is connected to the body unit through the second cable.

21. The biological signal processing unit according to claim 20, wherein the body unit includes a display, the biological signal processing unit is configured to process the biological signal measured by the sensor without displaying the processed biological signal, and the display of the body unit is configured to display the biological signal transmitted from the transmitter of the biological signal processing unit.

22. The biological signal processing unit according to claim 21, wherein the body unit is a portable touch-screen device, and the display is adapted to receive an operation from a user.

23. The biological signal processing unit according to claim 20, wherein the biological signal includes at least one of blood oxygen saturation (SpO2) data, electrocardiographic (ECG) data, and non-invasive blood pressure (NIBP) data.

24. The biological signal processing unit according to claim 20 further comprising a clip adapted to be attached to the patient.

25. The biological signal processing unit according to claim 20, wherein the signal processor is configured to cause a display of the body unit to display the biological signal in waveform data and numerical data.

26. The biological signal processing unit according to claim 25, wherein the at least one sensor is a blood oxygen saturation (SpO2) sensor, and the waveform data and the numerical data of SpO2 data measured by the SpO2 sensor is concurrently displayed on the display.

\* \* \* \* \*

UNITED STATES PATENT AND TRADEMARK OFFICE
CERTIFICATE OF CORRECTION

PATENT NO. : 10,952,610 B2
APPLICATION NO. : 13/015096
DATED : March 23, 2021
INVENTOR(S) : Hirokazu Ogino et al.

Page 1 of 1

It is certified that error appears in the above-identified patent and that said Letters Patent is hereby corrected as shown below:

In the Specification

Column 7, Line 15-16, "3b, and a third transmitting portion 3 and a temperature probe 3d." should read -- 3b, a third transmitting portion 3c, and a temperature probe 3d. --

Signed and Sealed this
Second Day of November, 2021

Drew Hirshfeld
*Performing the Functions and Duties of the*
*Under Secretary of Commerce for Intellectual Property and*
*Director of the United States Patent and Trademark Office*